(12) United States Patent
Chen et al.

(10) Patent No.: US 10,151,721 B2
(45) Date of Patent: Dec. 11, 2018

(54) WHOLE BLOOD MEASUREMENT METHOD ASSOCIATED TO HEMATOCRIT (HCT) AND WHOLE BLOOD MEASUREMENT CIRCUIT THEREOF

(71) Applicant: HOLTEK SEMICONDUCTOR INC., Hsinchu (TW)

(72) Inventors: Kuo-Hsiang Chen, Hsinchu (TW); Kuo-Yang Li, Hsinchu (TW); Hung-Yu Liu, Hsinchu (TW)

(73) Assignee: HOLTEK SEMICONDUCTOR INC., Hsinchu (TW)

( * ) Notice: Subject to any disclaimer, the term of this patent is extended or adjusted under 35 U.S.C. 154(b) by 98 days.

(21) Appl. No.: 15/221,821

(22) Filed: Jul. 28, 2016

(65) Prior Publication Data
US 2017/0350844 A1 Dec. 7, 2017

(30) Foreign Application Priority Data
Jun. 6, 2016 (TW) .............................. 105117886 A

(51) Int. Cl.
*G01N 27/22* (2006.01)
*G01N 33/80* (2006.01)
*G01N 27/327* (2006.01)

(52) U.S. Cl.
CPC ........ *G01N 27/221* (2013.01); *G01N 27/3274* (2013.01); *G01N 33/80* (2013.01)

(58) Field of Classification Search
CPC . A61B 5/0022; A61B 5/02055; A61B 5/0402; A61B 5/0488; A61B 5/681; A61B 8/565; A61B 5/1112; A61B 5/1118; A61B 8/0808; A61B 2562/0219; A61B 5/0008; A61B 5/0006; A61B 5/0476; A61B 5/1117; A61B 5/002; G01N 2015/1006; G01N 2021/513; G01N 2021/6417; G01N 2021/6441; G01N 2035/00326; G01N 2035/00495; G01N 21/07; G01N 21/51; G01N 21/6428; G01N 21/66; G01N 21/75; G01N 21/76; G01N 21/78; G01N 27/221; G01N 27/3274; G01N 33/50; G01N 33/80; G01N 35/00; G01N 35/0092; G01N 35/1065; G01N 35/1095
See application file for complete search history.

(56) References Cited

U.S. PATENT DOCUMENTS

2014/0178909 A1 6/2014 Tonks
2015/0153298 A1 6/2015 Chen et al.

FOREIGN PATENT DOCUMENTS

| GB | 2425843 A | 11/2006 |
| JP | S5790158 A | 6/1982 |
| JP | S5913948 A | 1/1984 |
| JP | 2008046141 A | 2/2008 |
| JP | 2008508078 A | 3/2008 |
| JP | 2008215901 A | 9/2008 |

OTHER PUBLICATIONS

European Patent Office Search Report issued in corresponding EP patent application dated Oct. 20, 2017.
Office Action issued in corresponding Japan patent application dated Aug. 1, 2017.

*Primary Examiner* — Deborah K Ware
(74) *Attorney, Agent, or Firm* — Rabin & Berdo, P.C.

(57) ABSTRACT

A whole blood measurement method associated to hematocrit (HCT) and a whole blood measurement circuit thereof is applied in the detection of HCT of a whole blood sample to be tested. Herein, a time to digital converting circuit (TDC) is used for counting charging time or discharging time of a fixed capacitor and a to-be-tested sample, and a capacitance difference that is related to HCT is generated according to the charging time or the discharging time, so as to provide a reference for a whole blood feature test.

6 Claims, 9 Drawing Sheets

WHOLE BLOOD MEASUREMENT METHOD ASSOCIATED TO HEMATOCRIT (HCT) AND WHOLE BLOOD MEASUREMENT CIRCUIT THEREOF

CROSS-REFERENCES TO RELATED APPLICATIONS

This non-provisional application claims priority under 35 U.S.C. § 119(a) on Patent Application No. 105117886 filed in Taiwan, R.O.C. on Jun. 6, 2016, the entire contents of which are hereby incorporated by reference.

BACKGROUND

Technical Field

The present invention relates to a blood test technology, and in particular, to a whole blood measurement method associated to hematocrit (HCT) and a whole blood measurement circuit thereof.

Related Art

In blood test procedures of common large hospitals or medical centers, first, blood cells are separated from plasma by using a centrifuge, and then various types of tests are carried out on the plasma, so as to ensure the accuracy of test results. A home detector performs measurement by directly using whole blood, and has advantages of low blood volume, low cost, rapid detection, and portability. However, the measurement performed by using whole blood causes that an error of a current blood glucose meter exceeds a standard, and accuracy of a blood glucose test is reduced. May studies show that hematocrit (HCT) is a vital factor that affects a blood glucose test.

HCT is the volume percentage of red blood cells in blood. Generally, the HCT of male blood is about 36% to 50%, and the HCT of female blood is about 34% to 47%. People can know quality of blood according to the HCT in blood. When blood glucose concentration of blood is measured, a measurement value of the blood glucose concentration also varies with the HCT.

There are many methods for measuring the HCT, for example, the HCT may be calculated by using an approach of measuring blood impedance, by using an optical approach, by using a redox reaction approach, and by using an electrochemical approach. Using a measurement method that uses a redox reaction approach as an example, in an electrochemical test strip, a redox substance needs to be provided on a counter electrode, so as to generate an obvious redox current, thereby measuring the HCT. However, there is room for further improvement of the HTC measurement method in the prior art.

SUMMARY

In an embodiment, a whole blood measurement method associated to hematocrit (HCT) includes: counting a first charging time for charging a fixed capacitor to a predetermined potential; converting the first charging time to a first digital signal by using a time to digital converting circuit (TDC); counting a second charging time for charging a to-be-tested sample to the predetermined potential; converting the second charging time to a second digital signal by using the TDC; and generating a capacitance difference according to the first digital signal, the second digital signal, and a capacitance of the fixed capacitor.

In another embodiment, a whole blood measurement method associated to HCT includes: charging a fixed capacitor to a power supply potential by using a power supply circuit; counting a first discharging time for discharging the fixed capacitor from the power supply potential to a predetermined potential; converting the first discharging time to a first digital signal by using a TDC; charging a to-be-tested sample to the power supply potential by using the power supply circuit; counting a second discharging time for discharging the to-be-tested sample from the power supply potential to the predetermined potential; converting the second discharging time to a second digital signal by using the TDC; and generating a capacitance difference according to the first digital signal, the second digital signal, and a capacitance of the fixed capacitor.

In an embodiment, a whole blood measurement circuit associated to HCT includes: a power supply circuit, a fixed capacitor, a first measurement end, a second measurement end, a charging switch, a first switch, a second switch, a TDC, and a processing unit. The first measurement end and the second measurement end are configured to couple a to-be-tested sample. The charging switch is coupled between the power supply circuit and a first end of the fixed capacitor, and is coupled between the power supply circuit and the first measurement end. The first switch is coupled between a second end of the fixed capacitor and ground. The second switch is coupled between the second measurement end and the ground. The processing unit is coupled to the charging switch, the first switch, the second switch, and the TDC. The processing unit is configured to control the charging switch, the first switch, and the second switch so as to separately charge the fixed capacitor and the to-be-tested sample. The TDC is configured to count a first charging time for charging the fixed capacitor to a predetermined potential and convert the first charging time to a first digital signal, and count a second charging time for charging the to-be-tested sample to the predetermined potential and convert the second charging time to a second digital signal. Then, the processing unit is further configured to generate a capacitance difference according to the first digital signal, the second digital signal, and a capacitance of the fixed capacitor.

In another embodiment, a whole blood measurement circuit associated to HCT includes: a power supply circuit, a fixed capacitor, a first measurement end, a second measurement end, a charging switch, a first switch, a second switch, a discharging resistor, a discharging switch, a TDC, and a processing unit. The first measurement end and the second measurement end are configured to couple a to-be-tested sample. The charging switch is coupled between the power supply circuit and a first end of the fixed capacitor, and is coupled between the power supply circuit and the first measurement end. The first switch is coupled between a second end of the fixed capacitor and ground. The second switch is coupled between the second measurement end and the ground. A first end of the discharging resistor is coupled to the first end of the fixed capacitor and the first measurement end. The discharging switch is coupled between a second end of the discharging resistor and the ground. The processing unit is coupled to the charging switch, the first switch, the second switch, the discharging switch, and the TDC. The processing unit is configured to control the charging switch, the first switch, the second switch, and the discharging switch so as to separately charge and discharge the fixed capacitor and the to-be-tested sample. The TDC is configured to count a first discharging time for discharging the fixed capacitor to a predetermined potential and convert the first discharging time to a first digital signal, and count a second discharging time for discharging the to-be-tested sample to the predetermined potential and convert the second discharging time to a second digital signal. Then, the processing unit is further configured to generate a capacitance difference according to the first digital signal, the second digital signal, and a capacitance of the fixed capacitor.

To sum up, according to the embodiments, the whole blood measurement method associated to HCT and the whole blood measurement circuit thereof is applied in detection of HCT of a whole blood sample to be tested, so as to provide a calibration reference for a blood feature (e.g. blood glucose) of a whole blood test, and further implement a blood test with low blood volume, low cost, and high accuracy.

BRIEF DESCRIPTION OF THE DRAWINGS

The present invention will become more fully understood from the detailed description given herein below for illustration only, and thus are not limitative of the present invention, and wherein.

DETAILED DESCRIPTION

Figure 1:
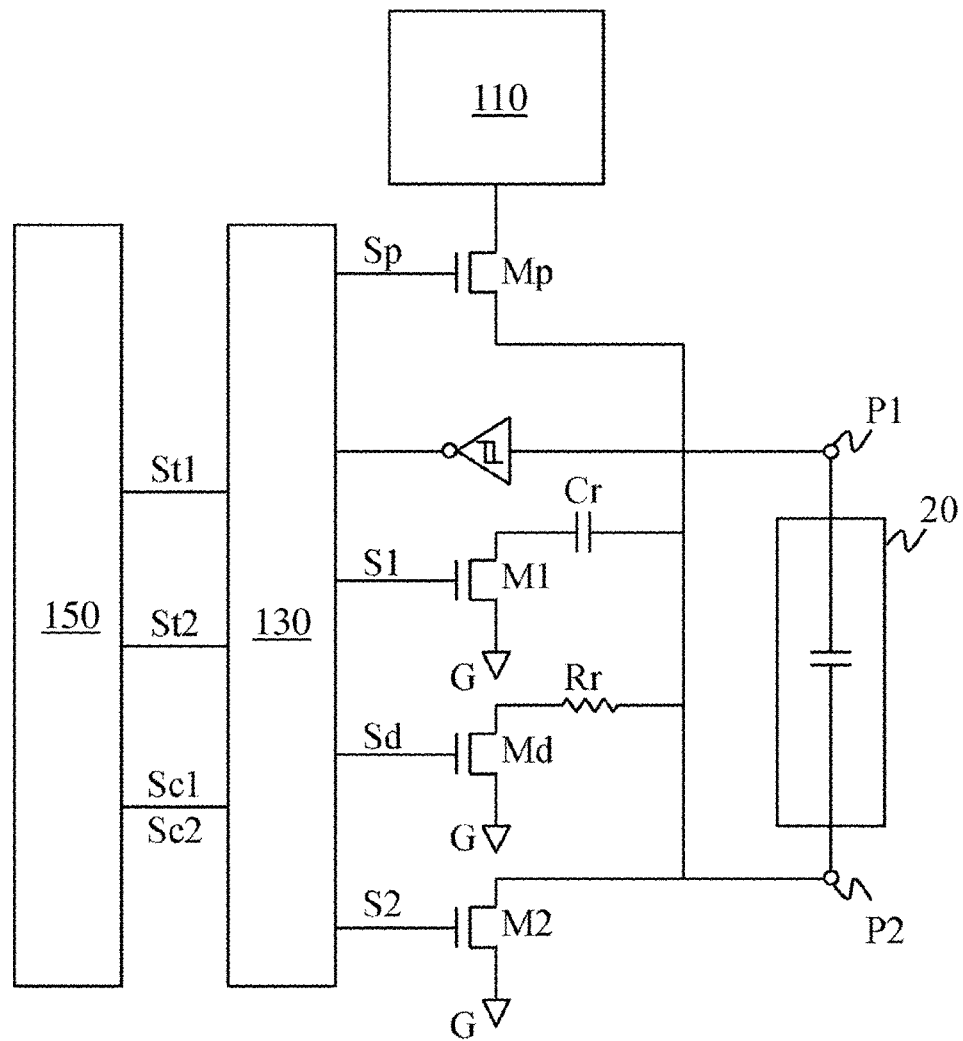
FIG. 1 is a schematic diagram of an embodiment of a whole blood measurement circuit associated to hematocrit (HCT) according to the present invention.

FIG. 1 is a schematic diagram of an embodiment of a whole blood measurement circuit associated to hematocrit (HCT) according to the present invention. Referring to FIG. 1, a whole blood measurement circuit associated to HCT includes: a power supply circuit 110, a fixed capacitor Cr, a first measurement end P1, a second measurement end P2, a charging switch Mp, a first switch M1, a second switch M2, a processing unit 130, and a time to digital converting circuit (TDC) 150.

The charging switch Mp is coupled between the power supply circuit 110 and a first end of the fixed capacitor Cr, and is coupled between the power supply circuit 110 and the first measurement end P1. The first switch M1 is coupled between a second end of the fixed capacitor Cr and ground G. The second switch M2 is coupled between the second measurement end P2 and the ground G. The processing unit 130 is coupled to the charging switch Mp, the first switch M1, the second switch M2, and the TDC 150. In other words, a first end of the charging switch Mp is coupled to a power supply end of the power supply circuit 110. A second end of the charging switch Mp is coupled to the first end of the fixed capacitor Cr and the first measurement end P1. A control end of the charging switch Mp is coupled to the processing unit 130. A first end of the first switch M1 is coupled to the second end of the fixed capacitor Cr. A second end of the first switch M1 is coupled to the ground G. A control end of the first switch M1 is coupled to the processing unit 130. A first end of the second switch M2 is coupled to the second measurement end P2. A second end of the second switch M2 is coupled to the ground G. A control end of the second switch M2 is coupled to the processing unit 130. In addition, the processing unit 130 is electrically connected to the first end of the fixed capacitor Cr and the first measurement end P1. During measurement, a to-be-tested sample 20 is removably coupled between the first measurement end P1 and the second measurement end P2. At this time, the to-be-tested sample 20 is equivalent to a to-be-tested capacitor connected between the first measurement end P1 and the second measurement end P2. In other words, an HCT change in blood (the to-be-tested sample 20) is equivalent to a capacitive effect.

Figure 2:
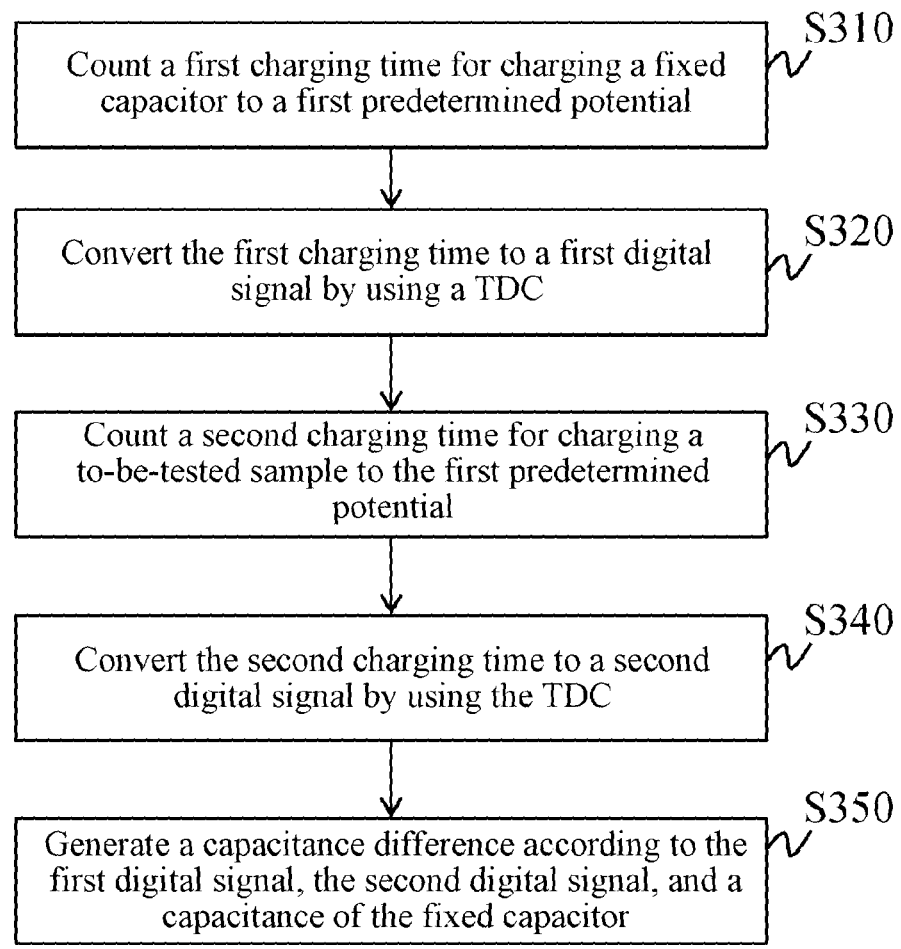
FIG. 2 is a flowchart of a first embodiment of a whole blood measurement method associated to HCT according to the present invention.
Figure 3:
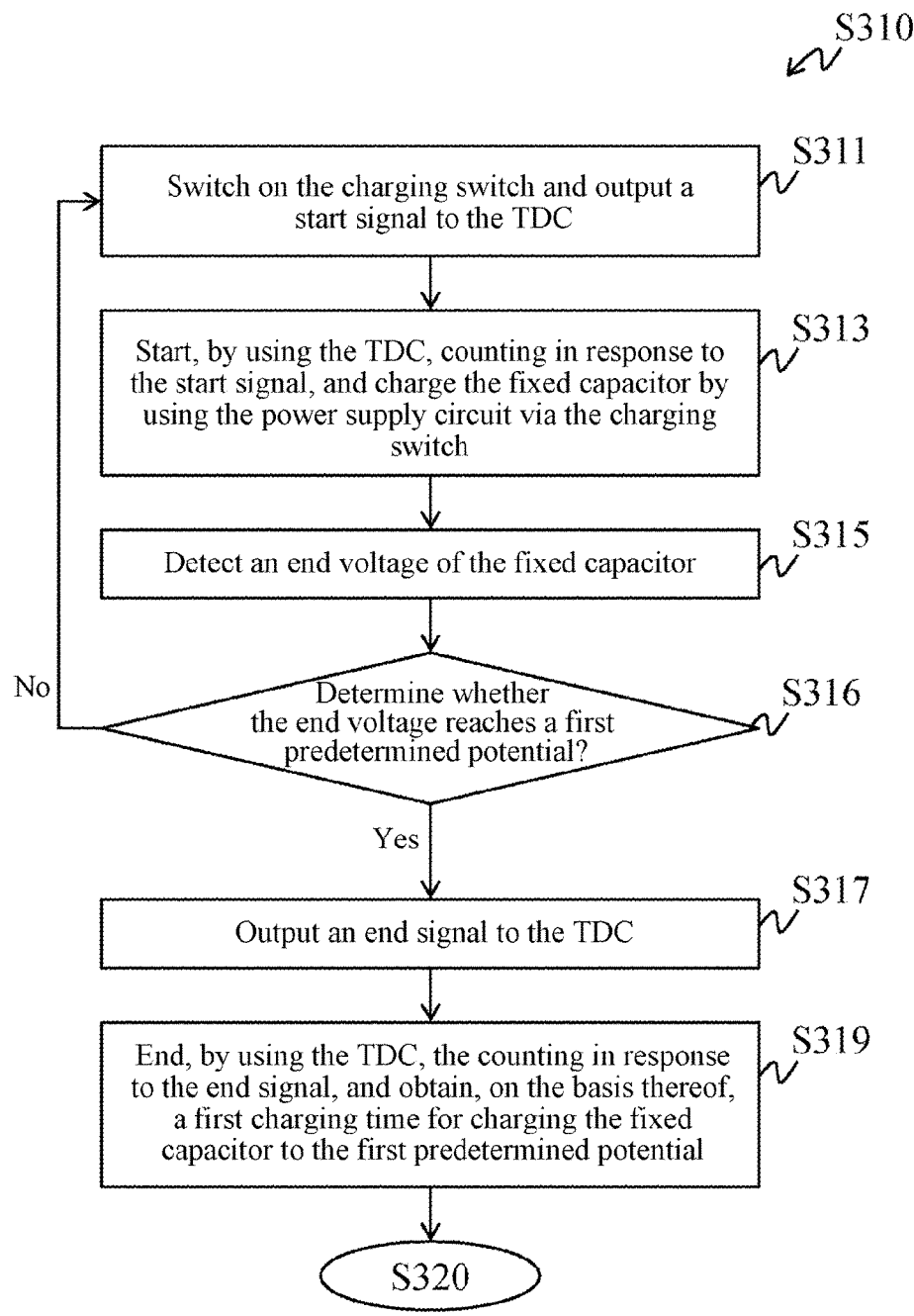
FIG. 3 is a flowchart of an embodiment of step S310 in FIG. 2.
Figure 4:
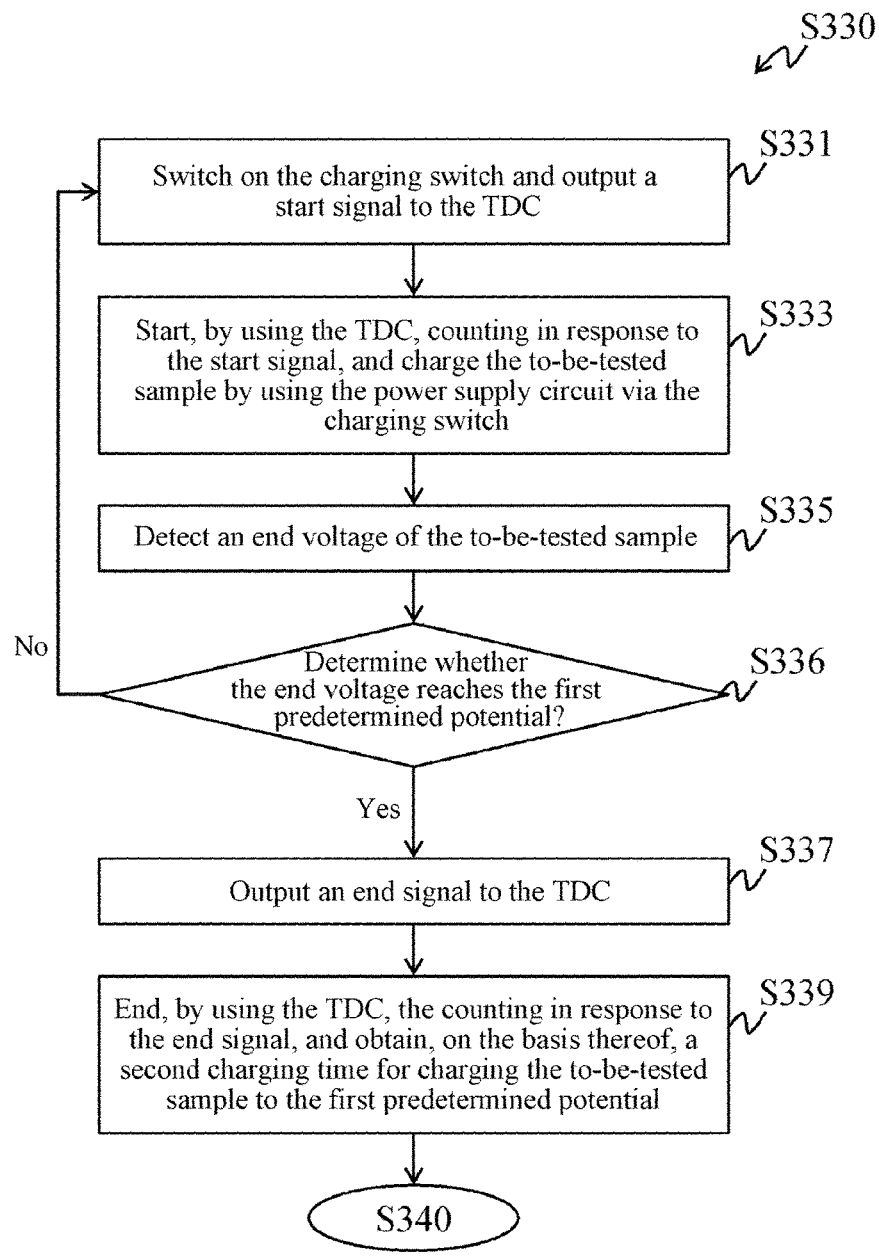
FIG. 4 is a flowchart of an embodiment of step S330 in FIG. 2.

FIG. 2 is a flowchart of a first embodiment of a whole blood HCT measurement method associated to HCT according to the present invention. FIG. 3 is a flowchart of an embodiment of step S310 in FIG. 2. FIG. 4 is a flowchart of an embodiment of step S330 in FIG. 2.

In an embodiment, referring to FIG. 1 to FIG. 4, the processing unit 130 outputs control signals Sp and S1 to control the charging switch Mp and the first switch M1 to be switched on (on), and simultaneously outputs a start signal S0 to the TDC 150 (step S311), so as to enable the power supply circuit 110 to start charging the fixed capacitor Cr, and enable the TDC 150 to start counting in response to the start signal S0 (step S313). At this time, the second switch M2 is switched off. After the charging switch Mp and the first switch M1 are switched on, the power supply circuit 110 charges the fixed capacitor Cr via the charging switch Mp, and the TDC 150 simultaneously starts the counting. In a charging process, the processing unit 130 detects an end voltage of the fixed capacitor Cr (step S315), and determines whether the end voltage reaches a predetermined potential (hereinafter referred to as the first predetermined potential) (step S316). When the end voltage of the fixed capacitor Cr does not reach the first predetermined potential, the processing unit 130 keeps outputting the control signals Sp and S1, so as to enable the charging switch Mp and the first switch M1 to maintain switched on. When the end voltage of the fixed capacitor Cr reaches the first predetermined potential, the processing unit 130 outputs an end signal St2 to the TDC 150 (step S317). At this time, the TDC 150 ends the counting in response to the end signal St2, and obtains, on the basis thereof, a first charging time for charging the fixed capacitor Cr to the first predetermined potential (step S319). At this time, the first charging time is a time difference between a time for receiving the start signal S0 and a time for receiving the end signal St2. The TDC 150 converts the first charging time to a first digital signal Sc1 (step S320) and transmits the first digital signal Sc1 to the processing unit 130.

Besides, the processing unit 130 outputs control signals Sp and S2 to control the charging switch Mp and the second switch M2 to be switched on (on), and simultaneously outputs a start signal S0 to the TDC 150 (step S331), so as to enable the power supply circuit 110 to start charging the to-be-tested sample 20, and enable the TDC 150 to start counting in response to the start signal S0 (step S333). At this time, the first switch M1 is switched off. After the charging switch Mp and the second switch M2 are switched on, the power supply circuit 110 charges the to-be-tested sample 20 via the charging switch Mp, and the TDC 150 simultaneously starts the counting. In a charging process, the processing unit 130 detects an end voltage of the to-be-tested sample 20 (step S335), and determines whether the end voltage reaches the first predetermined potential (step S336). When the end voltage of the to-be-tested sample 20 does not reach the first predetermined potential, the processing unit 130 keeps outputting the control signals Sp and S2, so as to enable the charging switch Mp and the second switch M2 to maintain switched on. When the end voltage of the to-be-tested sample 20 reaches the first predetermined potential, the processing unit 130 outputs an end signal St2 to the TDC 150 (step S337). At this time, the TDC 150 ends the counting in response to the end signal St2, and obtains, on the basis thereof, a second charging time for charging the to-be-tested sample 20 to the first predetermined potential (step S339). At this time, the second charging time is a time difference between a time for receiving the start signal S0 and a time for receiving the end signal St2. The TDC 150 converts the second charging time to a second digital signal Sc2 (step S340) and transmits the second digital signal Sc2 to the processing unit 130.

After receiving the first digital signal Sc1 and the second digital signal Sc2, the processing unit 130 generates a capacitance difference according to the first digital signal, the second digital signal, and a capacitance of the fixed capacitor Cr (step S350). In some embodiments, a processing unit 130 may estimate a capacitance difference according a change between the first digital signal and the second digital signal, and a capacitance of the fixed capacitor Cr. At this time, the obtained capacitance difference is related to the HCT of the to-be-tested sample 20.

In some embodiments, a first predetermined potential and a capacitance of a fixed capacitor Cr are pre-stored in a storage unit (not shown in the figures). When a processing unit 130 needs to use a value, the processing unit 130 reads, from the storage unit, the value that needs to be used (the first predetermined potential or the capacitance of the fixed capacitor Cr). The storage unit may be built in the processing unit 130, or may be located outside the processing unit 130 and is electrically connected to the processing unit 130.

In some embodiments, a whole blood measurement circuit associated to HCT may further include a discharging resistor Rr and a discharging switch Md. A first end of the discharging resistor Rr is coupled to a first end of a fixed capacitor Cr and a first measurement end P1. The discharging switch Md is coupled between a second end of the discharging resistor Rr and ground G. That is, a first end of the discharging switch Md is coupled to the second end of the discharging resistor Rr. A second end of the discharging switch Md is coupled to the ground G. A control end of the discharging switch Md is coupled to a processing unit 130.

After each time when charging is completed, the processing unit 130 outputs a control signal Sd to control the discharging switch Md to be switched on (on), so as to discharge the charged fixed capacitor Cr or the charged to-be-tested sample 20.

In another embodiment, a capacitance difference may be obtained by measuring a discharging time.

Figure 5:
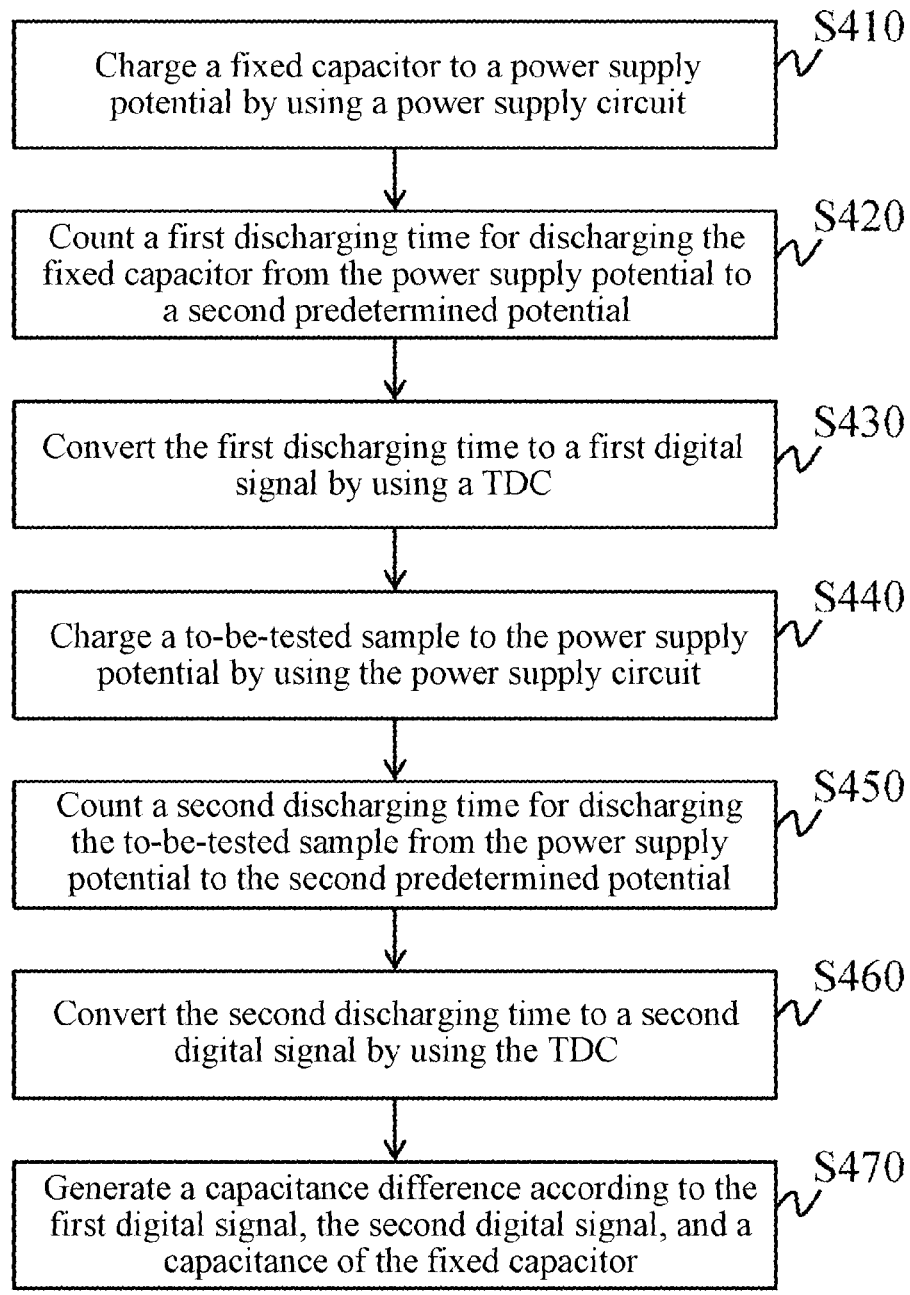
FIG. 5 is a flowchart of a second embodiment of the whole blood measurement method associated to HCT according to the present invention.
Figure 6:
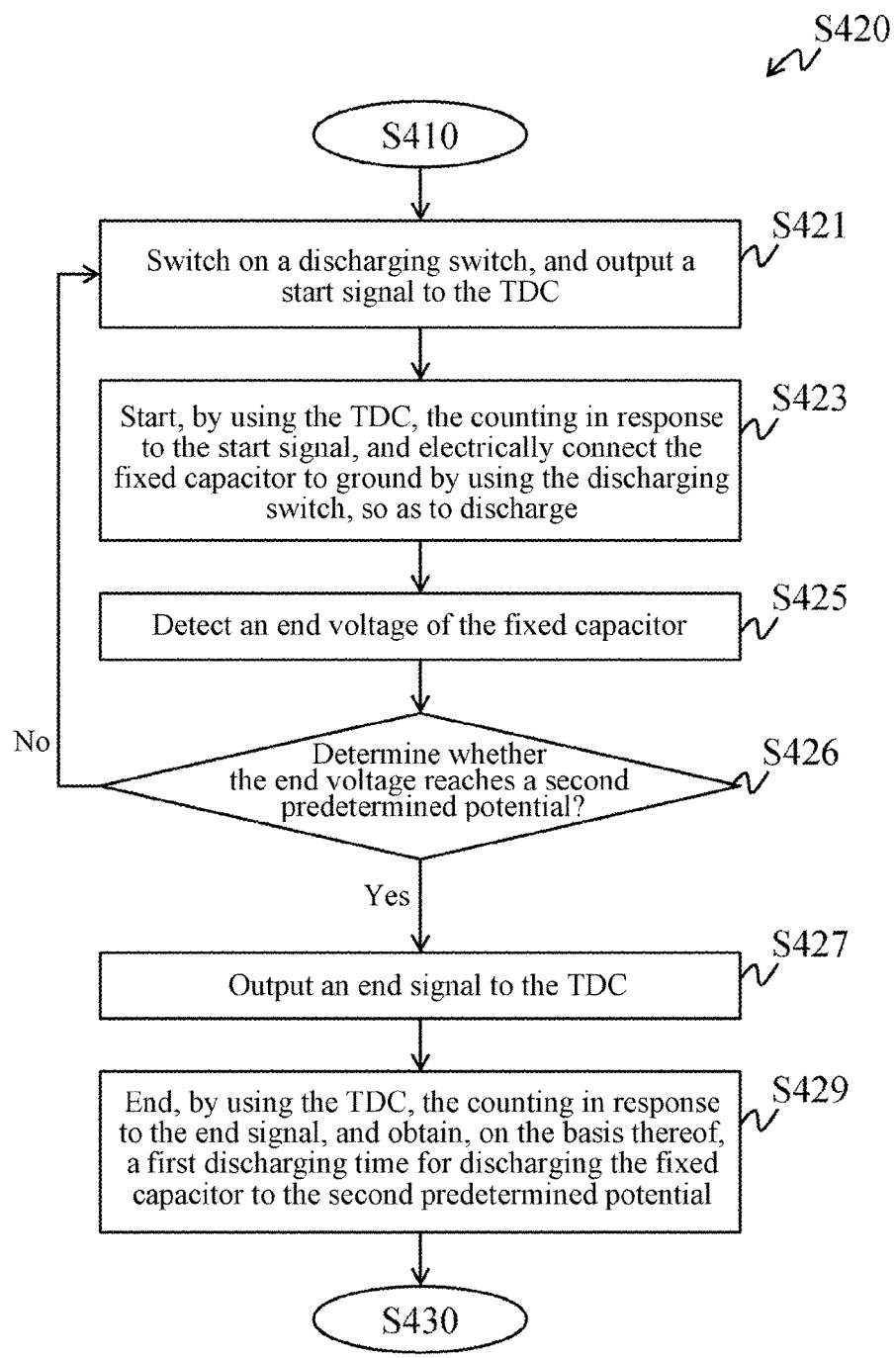
FIG. 6 is a flowchart of an embodiment of step S420 in FIG. 5.
Figure 7:
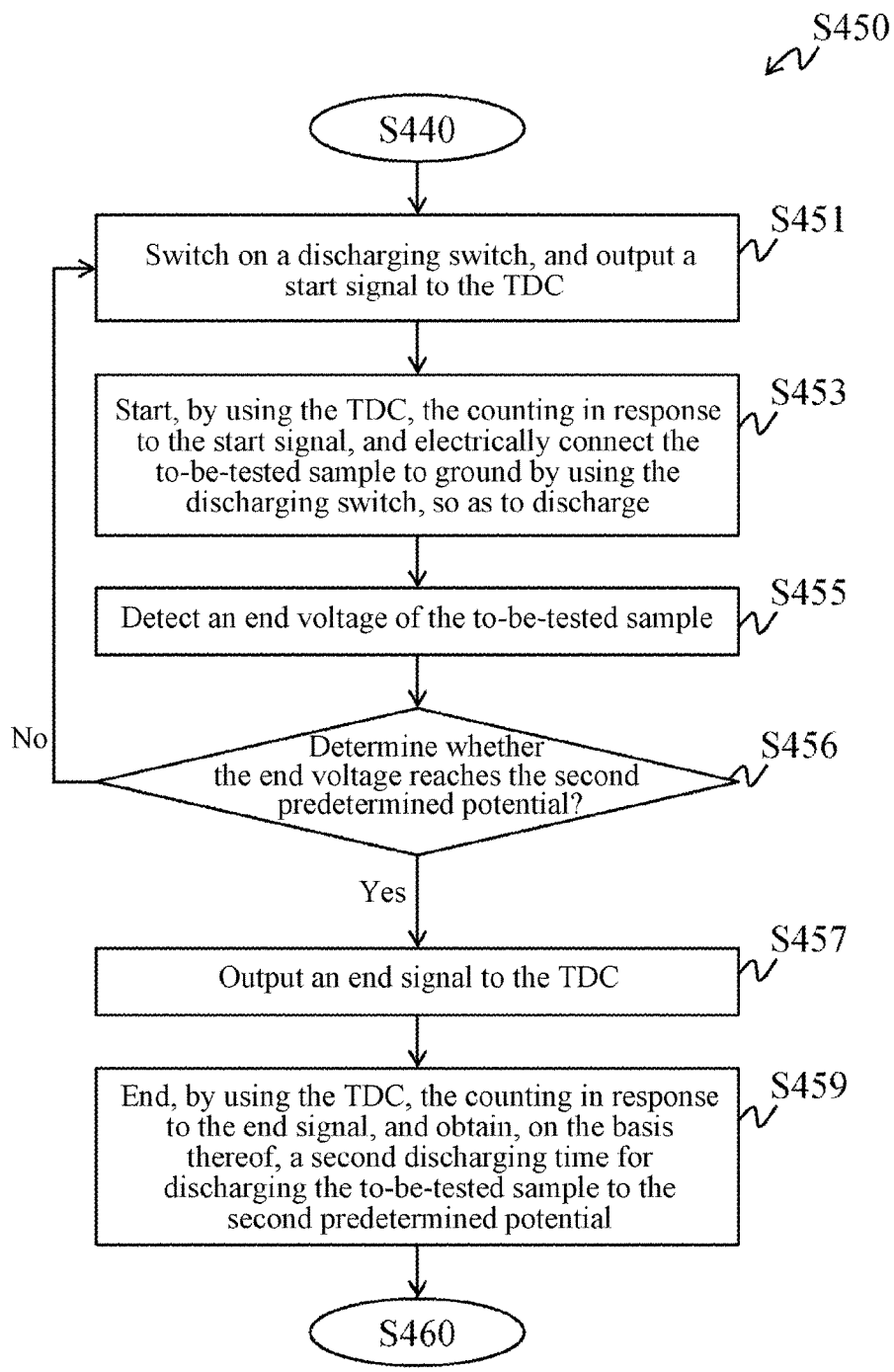
FIG. 7 is a flowchart of an embodiment of step S450 in FIG. 5.

FIG. 5 is a flowchart of a second embodiment of the whole blood measurement method associated to HCT according to the present invention. FIG. 6 is a flowchart of an embodiment of step S420 in FIG. 5. FIG. 7 is a flowchart of an embodiment of step S450 in FIG. 5.

In another embodiment, referring to FIG. 1 and FIG. 5 to FIG. 7, a processing unit 130 outputs control signals Sp and S1 to control a charging switch Mp and a first switch M1 to be switched on (on), so as to enable a power supply circuit 110 to start charging a fixed capacitor Cr. At this time, both a second switch M2 and a discharging switch Md are switched off. After the charging switch Mp and the first switch M1 are switched on, the power supply circuit 110 charges the fixed capacitor Cr via the charging switch Mp, so as to enable the fixed capacitor Cr to be charged to a power supply potential (step S410). In some embodiments, a processing unit 130 may control a time for charging, by a power supply circuit 110, a fixed capacitor Cr by controlling switch on times of a charging switch Mp and a first switch M1, so as to enable the power supply circuit 110 to charge the fixed capacitor Cr to a power supply potential. For example, the processing unit 130 keeps outputting control signals Sp and S1 for a predetermined time. The predetermined time is sufficient to enable the power supply circuit 110 to charge the fixed capacitor Cr to the power supply potential. The processing unit 130 stops outputting the control signals Sp and S1 after the predetermined time, so as to enable the charging switch Mp and the first switch M1 to be switched off (off). In some embodiments, a processing unit 130 may control a time for charging, by a power supply circuit 110, a fixed capacitor Cr by detecting whether an end voltage of the fixed capacitor Cr reaches a power supply potential, so as to control the power supply circuit 110 to charge the fixed capacitor Cr to the power supply potential. For example, when the end voltage of the fixed capacitor Cr does not reach the power supply potential, the processing unit 130 keeps outputting control signals Sp and S1, so as to enable a charging switch Mp and a first switch M1 to maintain switched on. When the end voltage of the fixed capacitor Cr reaches the power supply potential, the processing unit 130 stops outputting the control signals Sp and S1, so as to enable the charging switch Mp and the first switch M1 to be switched off.

After the fixed capacitor Cr is charged to the power supply potential, the processing unit 130 outputs a control signal Sd to control the discharging switch Md to be switched on (on), and simultaneously outputs a start signal S0 to the TDC 150 (step S421), so as to enable the fixed capacitor Cr to be electrically connected to ground via the discharging resistor Rr and the discharging switch Md and to be discharged, and enable the TDC 150 to start counting in response to the start signal S0 (step S423). At this time, the charging switch Mp, the first switch M1, and the second switch M2 are all switched off. In a discharging process, the processing unit 130 detects an end voltage of the fixed capacitor Cr (step S425), and determines whether the end voltage reaches a predetermined potential (hereinafter referred to as the second predetermined potential) (step S426). When the end voltage of the fixed capacitor Cr does not reach the second predetermined potential, the processing unit 130 keeps outputting the control signal Sd, so as to enable the discharging switch Md to maintain switched on. When the end voltage of the fixed capacitor Cr reaches the second predetermined potential, the processing unit 130 outputs an end signal St2 to the TDC 150 (step S427). At this time, the TDC 150 ends the counting in response to the end signal St2, and obtains, on the basis thereof, a first discharging time for discharging the fixed capacitor Cr to the second predetermined potential (step S429). At this time, the first discharging time is a time difference between a time for receiving the start signal S0 and a time for receiving the end signal St2. The TDC 150 converts the first discharging time to a first digital signal Sc1 (step S430) and transmits the first digital signal Sc1 to the processing unit 130.

Besides, the processing unit 130 outputs control signals Sp and S2 to control the charging switch Mp and the second switch M2 to be switched on (on), so as to enable the power supply circuit 110 to start charging the to-be-tested sample 20. At this time, both the first switch M1 and the discharging switch Md are switched off. After the charging switch Mp and the second switch M2 are switched on, the power supply circuit 110 charges the to-be-tested sample 20 via the charging switch Mp, so as to enable the to-be-tested sample 20 to be charged to the power supply potential (step S440). In some embodiments, a processing unit 130 may control a time for charging, by a power supply circuit 110, a to-be-tested sample 20 by controlling switch on times of a charging switch Mp and a second switch M2, so as to enable the power supply circuit 110 to charge the to-be-tested sample 20 to a power supply potential. For example, the processing unit 130 keeps outputting control signals Sp and S2 for a predetermined time. The predetermined time is sufficient to enable the power supply circuit 110 to charge the to-be-tested sample 20 to the power supply potential. The processing unit 130 stops outputting the control signals Sp and S2 after the predetermined time, so as to enable the charging switch Mp and the second switch M2 to be switched off (off). In some embodiments, a processing unit 130 may control a time for charging, by a power supply circuit 110, a to-be-tested sample 20 by detecting whether an end voltage of the to-be-tested sample 20 reaches a power supply potential, so as to control the power supply circuit 110 to charge the to-be-tested sample 20 to the power supply potential. For example, when the end voltage of the to-be-tested sample 20 does not reach the power supply potential, the processing unit 130 keeps outputting the control signals Sp and S2, so as to enable the charging switch Mp and the second switch M2 to maintain switched on. When the end voltage of the to-be-tested sample 20 reaches the power supply potential, the processing unit 130 stops outputting the control signals Sp and S2, so as to enable the charging switch Mp and the second switch M2 to be switched off.

After the to-be-tested sample 20 is charged to the power supply potential, the processing unit 130 outputs a control signal Sd to control the discharging switch Md to be switched on (on), and simultaneously outputs a start signal S0 to the TDC 150 (step S451), so as to enable the to-be-tested sample 20 to be electrically connected to ground via the discharging resistor Rr and the discharging switch Md and to be discharged, and enable the TDC 150 to start counting in response to the start signal S0 (step S453). At this time, the charging switch Mp, the first switch M1, and the second switch M2 are all switched off. In a discharging process, the processing unit 130 detects an end voltage of the to-be-tested sample 20 (step S455), and determines whether the end voltage reaches the second predetermined potential (step S456). When the end voltage of the to-be-tested sample 20 does not reach the second predetermined potential, the processing unit 130 keeps outputting the control signal Sd, so as to enable the discharging switch Md to maintain switched on. When the end voltage of the to-be-tested sample 20 reaches the second predetermined potential, the processing unit 130 outputs an end signal St2 to the TDC 150 (step S457). At this time, the TDC 150 ends the counting in response to the end signal St2, and obtains, on the basis thereof, a second discharging time for discharging the to-be-tested sample 20 to the second predetermined potential (step S459). At this time, the second discharging time is a time difference between a time for receiving the start signal S0 and a time for receiving the end signal St2. The TDC 150 converts the second discharging time to a second digital signal Sc2 (step S460) and transmits the second digital signal Sc2 to the processing unit 130.

After receiving the first digital signal Sc1 and the second digital signal Sc2, the processing unit 130 generates a capacitance difference according to the first digital signal, the second digital signal, and a capacitance of the fixed capacitor Cr (step S470). In some embodiments, a processing unit 130 may estimate a capacitance difference according a change between a first digital signal and a second digital signal, and a capacitance of a fixed capacitor Cr. At this time, the capacitance difference is related to the HCT of the to-be-tested sample 20.

In some embodiments, a second predetermined potential and a capacitance of a fixed capacitor Cr are pre-stored in a storage unit (not shown in the figures). When a processing unit 130 needs to use a value, the processing unit 130 reads, from the storage unit, the value that needs to be used (the second predetermined potential or the capacitance of the fixed capacitor Cr). The storage unit may be built in the processing unit 130, or may be located outside the processing unit 130 and is electrically connected to the processing unit 130.

Figure 8:
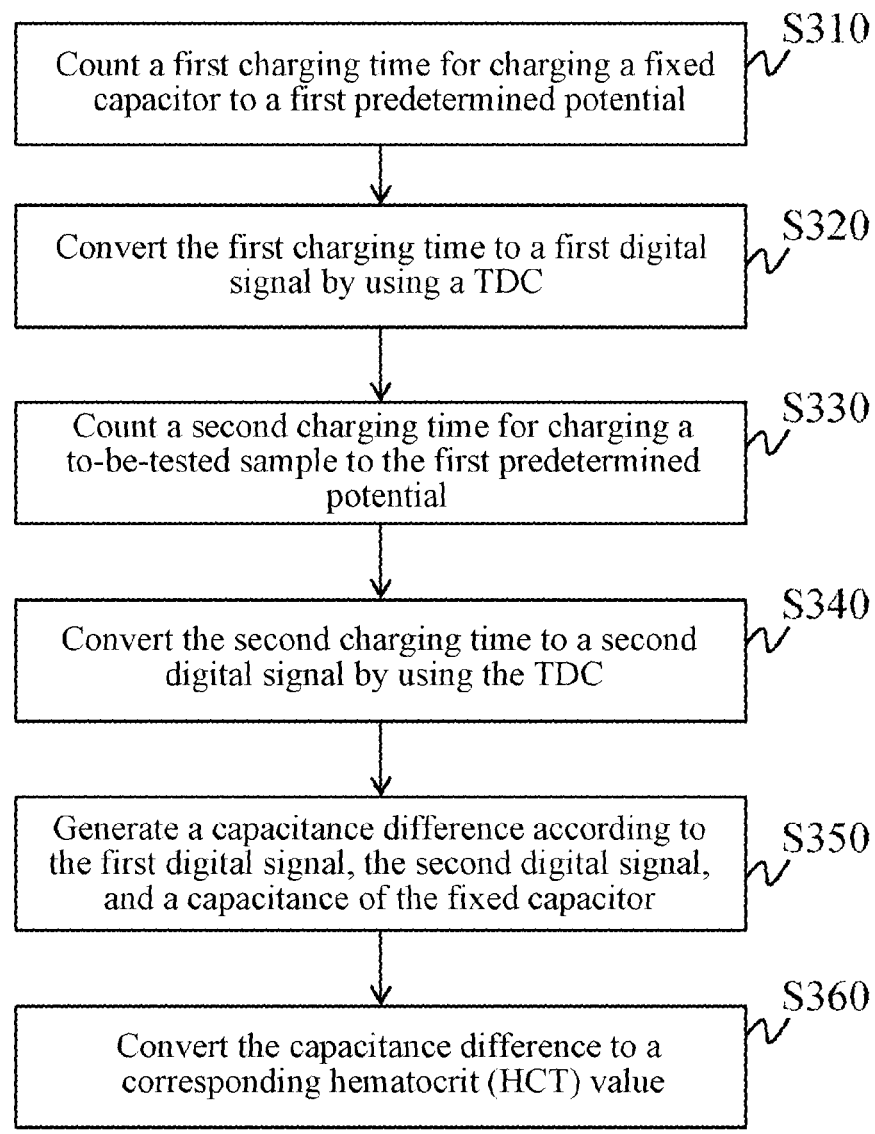
FIG. 8 is a flowchart of a third embodiment of the whole blood measurement method associated to HCT according to the present invention.
Figure 9:
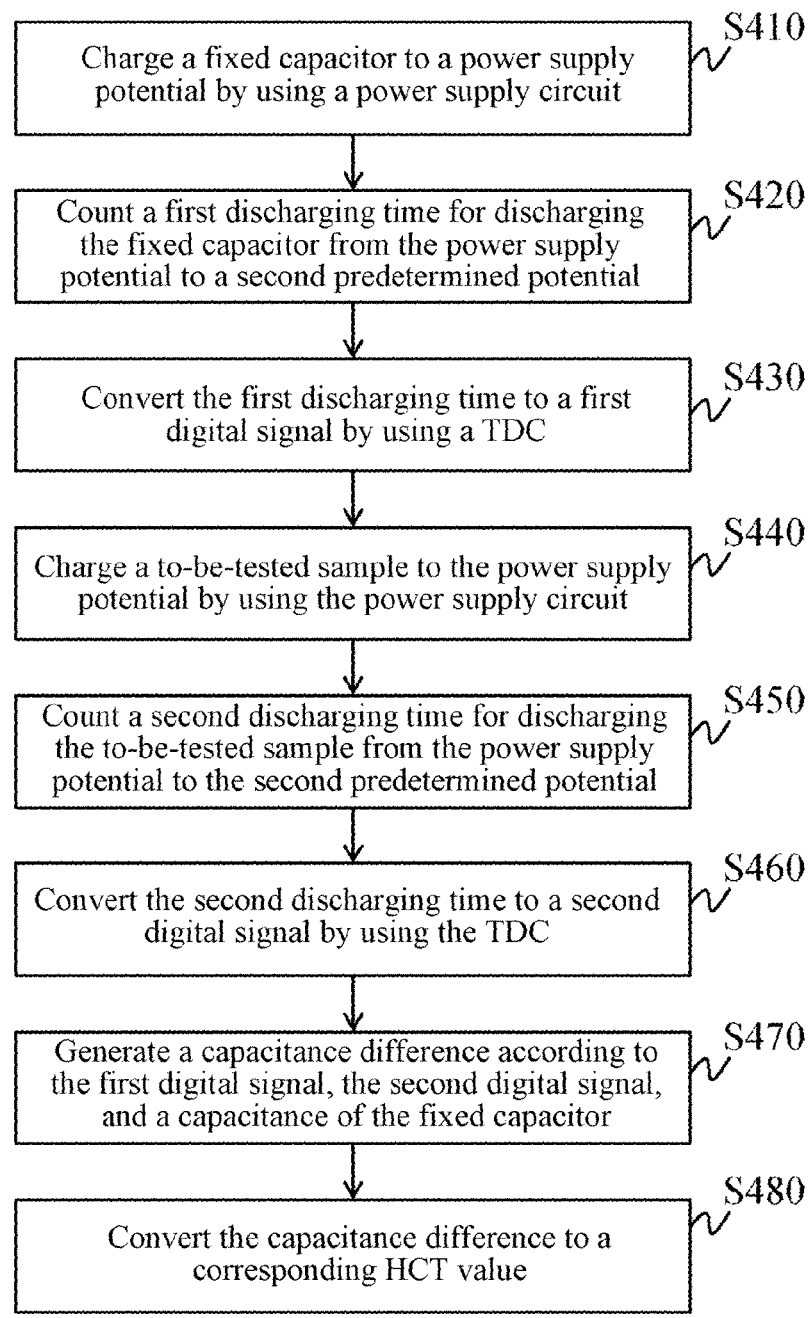
FIG. 9 is a flowchart of a fourth embodiment of the whole blood measurement method associated to HCT according to the present invention.

FIG. 8 is a flowchart of a third embodiment of the whole blood measurement method associated to HCT according to the present invention. FIG. 9 is a flowchart of a fourth embodiment of the whole blood measurement method associated to HCT according to the present invention.

In some embodiments, after a capacitance difference is obtained, a processing unit 130 may further convert the capacitance difference to a corresponding HCT value (step S360 or step S480), as shown in FIG. 8 and FIG. 9. In some embodiments, a processing unit 130 may convert a capacitance difference to a corresponding HCT value on the basis of a comparison table, a conversion curve, or a conversion formula. The comparison table, the conversion curve, or the conversion formula may be pre-stored in a storage unit (not shown in the figures).

It should be understood that execution sequences of steps are not limited to exemplary sequences shown in the drawings, the execution sequences may be appropriately adjusted according to execution content of the steps without departing from the spirit and scope of the present invention. For example: the counting of the charging time (or discharging time) of the to-be-tested sample is executed at first, and then the counting of the charging time (or discharging time) of the fixed capacitor is executed. Alternatively, the counting of the charging times (or discharging times) of the fixed capacitor and the to-be-tested sample can be simultaneously executed by using two groups of circuits.

In some embodiments, a to-be-tested sample 20 may be a blood glucose test strip. A processing unit 130 may be a microprocessor, a microcontroller, a digital signal processor, a micro-computer, a central processing unit, a field programmable gate array, a programmable logic device, a state machine, a logic circuit, an analog circuit, a digital circuit, and/or any apparatus for operating a signal (analog and/or digital) based on an operation instruction. The foregoing storage unit may be implemented by one or more storage elements. At this time, a storage element may be a memory, a working storage, or the like, for example, but is not limited herein.

To sum up, according to the embodiments, the whole blood measurement method associated to HCT and the whole blood measurement circuit thereof is applied in detection of HCT of a whole blood sample to be tested, so as to provide a calibration reference for a blood feature (e.g. blood glucose) of a whole blood test, and further implement a blood test with low blood volume, low cost, and high accuracy.

While the present disclosure has been described by way of example and in terms of the preferred embodiments, it is to be understood that the invention needs not be limited to the disclosed embodiments. For anyone skilled in the art, various modifications and improvements within the spirit of the instant disclosure are covered under the scope of the instant disclosure. The covered scope of the instant disclosure is based on the appended claims.

What is claimed is:

1. A whole blood measurement circuit associated to HCT, comprising:
   a power supply circuit;
   a fixed capacitor;
   a first measurement end;
   a second measurement end, configured to couple a to-be-tested sample along with the first measurement end;
   a charging switch, coupled between the power supply circuit and a first end of the fixed capacitor, and coupled between the power supply circuit and the first measurement end;
   a first switch, coupled between a second end of the fixed capacitor and ground;
   a second switch, coupled between the second measurement end and the ground;
   a TDC, configured to count a first charging time for charging the fixed capacitor to a predetermined potential and convert the first charging time to a first digital signal, and count a second charging time for charging the to-be-tested sample to the predetermined potential and convert the second charging time to a second digital signal; and
   a processing unit, coupled to the charging switch, the first switch, the second switch, and the TDC, configured to control the charging switch, the first switch, and the second switch so as to separately charge the fixed capacitor and the to-be-tested sample, and configured to generate a capacitance difference according to the first digital signal, the second digital signal, and a capacitance of the fixed capacitor.

2. The whole blood measurement circuit associated to HCT according to claim 1, wherein the processing unit is further configured to convert the capacitance difference to a corresponding HTC value.

3. The whole blood measurement circuit associated to HCT according to claim 1, wherein the to-be-tested sample is a blood glucose test strip.

4. A whole blood measurement circuit associated to HCT, comprising:
   a power supply circuit;
   a fixed capacitor;
   a first measurement end;
   a second measurement end, configured to couple a to-be-tested sample along with the first measurement end;
   a charging switch, coupled between the power supply circuit and a first end of the fixed capacitor, and coupled between the power supply circuit and the first measurement end;
   a first switch, coupled between a second end of the fixed capacitor and ground;
   a second switch, coupled between the second measurement end and the ground;
   a discharging resistor, wherein a first end of the discharging resistor is coupled to the first end of the fixed capacitor and the first measurement end;
   a discharging switch, coupled between a second end of the discharging resistor and ground;
   a TDC, configured to count a first discharging time for discharging the fixed capacitor to a predetermined potential and convert the first discharging time to a first digital signal, and count a second discharging time for discharging the to-be-tested sample to the predetermined potential and convert the second discharging time to a second digital signal; and
   a processing unit, coupled to the charging switch, the first switch, the second switch, the discharging switch, and the TDC, configured to control the charging switch, the first switch, the second switch, and the discharging switch so as to separately charge and discharge the fixed capacitor and the to-be-tested sample, and configured to generate a capacitance difference according to the first digital signal, the second digital signal, and a capacitance of the fixed capacitor.

5. The whole blood measurement circuit associated to HCT according to claim 4, wherein the processing unit is further configured to convert the capacitance difference to a corresponding HTC value.

6. The whole blood measurement circuit associated to HCT according to claim 4, wherein the to-be-tested sample is a blood glucose test strip.

* * * * *